United States Patent [19]

Ohno et al.

[11] Patent Number: 5,023,065
[45] Date of Patent: Jun. 11, 1991

[54] SYNTHETIC MICA POWDER, MANUFACTURING METHOD THEREOF AND COSMETICS HAVING THE SYNTHETIC MICA POWDER BLENDED THEREIN

[75] Inventors: Kazuhisa Ohno, Kanagawa; Tetsushi Kosugi, Aichi; Kenichiro Sugimori, Aichi; Akitsugu Ando, Aichi; Masaru Yamamoto, Aichi; Fukuji Suzuki; Masahiro Nakamura, both of Kanagawa; Nobuhisa Tsujita, Tokyo, all of Japan

[73] Assignees: Shiseido Co., Ltd.; Topy Kogyo K.K., both of Tokyo, Japan

[21] Appl. No.: 265,862
[22] PCT Filed: Jan. 26, 1988
[86] PCT No.: PCT/JP88/00059
    § 371 Date: Sep. 26, 1988
    § 102(e) Date: Sep. 26, 1988
[87] PCT Pub. No.: WO88/05453
    PCT Pub. Date: Jul. 28, 1988

[30] Foreign Application Priority Data

Jan. 26, 1987 [JP] Japan .................. 62-15676
Jan. 26, 1987 [JP] Japan .................. 62-15677
Jan. 26, 1987 [JP] Japan .................. 62-45678

[51] Int. Cl.$^5$ .............. C01B 33/20; C01B 33/25; C01B 33/34; C01B 33/32
[52] U.S. Cl. .................. 423/326; 156/647; 156/662; 423/327; 423/328; 423/332; 423/333
[58] Field of Search ............... 156/647, 662; 423/326, 423/327, 328, 328 C, 332, 333

[56] References Cited

U.S. PATENT DOCUMENTS 4,597,956 7/1986 Hinchey et al. ............... 423/328 C
4,766,099 8/1988 Dufresne et al. ............... 502/72

FOREIGN PATENT DOCUMENTS 58-45107 3/1983 Japan .

*Primary Examiner*—Olik Chaudhuri
*Assistant Examiner*—Lori F. Cuomo
*Attorney, Agent, or Firm*—Sughrue, Mion, Zinn, Macpeak & Seas

[57] ABSTRACT

The present invention concerns synthetic mica powder containing from 75 to 99% of the stoichiometrical composition of fluorine and/or having a shape in which the end face of particle is laminated, process for producing such synthetic mica powder, as well as cosmetics having synthetic mica powder blended therewith, in which the synthetic mica powder shows no leaching of fluorine ions and/or improved hold of oils due to lamination at the surface of powder. Accordingly, in this invention, cosmetics excellent in extensibility, gloss, adherence and modability, having appearance of high chroma and of high stability and safety can be obtained.

7 Claims, 2 Drawing Sheets

SYNTHETIC MICA POWDER, MANUFACTURING METHOD THEREOF AND COSMETICS HAVING THE SYNTHETIC MICA POWDER BLENDED THEREIN

TECHNICAL FIELD

The present invention concerns synthetic mica powder, production process therefor and cosmetics having the synthetic mica powder blended therewith. The cosmetics having the synthetic mica powder blended therewith according to the present invention have flowery outer-looking color, are excellent in property upon use, feeling of finish and highly stable and safety.

BACKGROUND ART

Various body pigments are blended with cosmetics with the aim of improving the extensibility, adherence, hiding power, moldability, etc. of products. As the body pigment, there can be mentioned inorganic powder such as talc, kaolin, and mica and organic powder such as nylon powder, polyethylene powder, polystyrene powder, acrylic resin powder and epoxy resin powder. Among them, mica has been used frequently since it has excellent transparent feeling, gloss and extensible feeling upon use. Recently, synthetic mica has been developed in addition to natural mica.

The synthetic mica is phyllosilicate minerals obtained by melting method, hydrothermal method or intersolid reaction method. Synthetic mica powder composed of good crystals has been prepared by mixing compounds each containing potassium, sodium, magnesium, aluminum, silicon and fluorine at a predetermined ratio, melting, crystallizing, cooling, and then mechanically pulverizing them. Such synthetic mica can include, for example, as below:

$KMg_3(AlSi_3O_{10})F_2$: potassium phlogopite
$KMg_{2\frac{1}{2}}(Si_4O_{10})F_2$: potassium tetrasilicon mica
$KMg_2Li(Si_4O_{10})F_2$: potassium taeniolite
$K_{\frac{2}{3}}Mg_{2\frac{2}{3}}Li_{\frac{1}{3}}(Si_4O_{10})F_2$
$NaMg_3(AlSi_3O_{10})F_2$: sodium phlogopite
$NaMg_2Li(Si_4O_{10})F_2$: sodium taeniolite
$NaMg_{2\frac{1}{2}}(Si_4O_{10})F_2$: sodium tetrasilicon mica
$Na_{\frac{1}{3}}Mg_{2\frac{2}{3}}Li_{\frac{1}{3}}(Si_4O_{10})F_2$: sodium hectorite As has been described above, although the mica has excellent properties, natural mica shows slight coloration since it contains a slight amount of metallic impurities. Accordingly, when the natural mica is blended with cosmetics, it tend to reduce the chroma of the outer looking color of the cosmetics. While organic pigments are used as an example of general means for improving the chroma of the outer looking color of the cosmetics, the organic pigment is poor in the light stability, and degraded by the light thereby causing undesirable phenomenon as cosmetics such as discoloration or disodoring.

Further, the mica has strong activity at the surface of powder, which tends to cause degradation in oils and perfumes.

In view of the extensible feeling upon use, spherical resin powder may be used as a substitute to some extent but, if the spherical resin powder is blended in a great amount, it reduces the adherence of cosmetics to skins and, further, worsens the moldability of cosmetics.

Referring to the gloss, it may be considered to blend titanium-mica type pearl pigment instead of mica, it also worsens the moldability of cosmetics.

In short, while mica has excellent properties that can not be substituted with other powders, optional blending thereof is inhibited at present in view of the coloration due to a slight amount of metals and surface activity.

Furthermore, mica has a drawback when blended with cosmetics that it is poor in oleophilicity, poor in dispersion stability and incapability of satisfying smooth feeling upon use.

That is, although the natural mica has excellent properties that can not be substituted with other powders, it involves a problem of coloration due to the slight amount of metallic impurities, the problem of surface activity and the problem of diffusion into the substrate, which inhibits the optional blending.

With an aim of overcoming such problems, the synthetic mica has been produced as described above. Since there is no incorporation of slight amount of metallic impurities in the synthetic mica, the problem of reducing the chroma of the outer-looking color of the cosmetics can be overcome. However, the activity at the surface of the powder is high as in the case of the natural mica. In addition, since fluorine ions ($F^-$) are leached out when blended in the cosmetic preparations, there is a safety problem. Furthermore, the oleophilicity is at the same level as the natural mica and the dispersion property or feeling upon use can not be improved.

In view of the above, it has keenly been demanded for the development of synthetic mica capable of suppressing the surface activity, with no leaching of fluorine ions and excellent in the dispersion property and feeling upon use, for the aim of producing cosmetics, particularly, make-up cosmetics excellent in extensibility, gloss, adherence and moldability, providing outer looking color at high chroma, and high stability and safety.

For overcoming these problems, the present inventors have tried regarding the mol number of F as follows:

(1) A method of dissolving F with strong acid.
(2) A method of synthesizing while decreasing the blending amount of F upon melting.
(3) A method of repeating washing with purified water, boiled water, etc.

However, not only F but also Mg, K, etc. are leached out in the same way to possibly destroy the structure in the method (1). Only the deposition amount of mica crystals is decreased and the mol number of F in the synthetic mica does not change in the method (2). No substantial effect can be obtained for the decrease of the mol number of F by the method (3).

For improving the oleophilicity, it has been considered to improve the hold of oils by making the surface shape of the synthetic mica particles more irregular and there have been tried those methods of vibration treatment using supersonic waves, chemical treatment using oxidizing or reducing agent and treating with strong alkali. However, none of the methods has been effective and, rather, undesirably resulted in coarse powder due to secondary coagulation, etc.

DISCLOSURE OF INVENTION

In view of the above, the present inventors have made a further research and as a result of the earnest study have succeeded in the development of novel synthetic mica showing extremely useful and interesting natures and the production process therefor, and have attained the present invention.

That is, the first invention concerns synthetic mica powder in which the mol number of fluorine in the synthetic mica composition is from 75 to 99% of the stoichiometrical composition of synthetic mica, the second invention concerns synthetic mica powder in which the end face of the particle of synthetic mica powder has a laminated shape, the third invention concerns synthetic mica powder in which the mol number of fluorine in the synthetic mica composition is from 75 to 99% of theoretical composition of the synthetic mica and the end face of the particle of the synthetic mica powder has a laminated shape, the fourth invention concerns a production process for the synthetic mica powder of the first invention, in which synthetic mica is heat-treated at 600°–1350° C., the fifth invention concerns a production process for the synthetic mica powder of the second invention, in which the synthetic mica powder is brought into contact with an aqueous solution comprising one or more of acid or chelating agent, the sixth invention concerns a production process for the synthetic mica of the third invention, which comprises in combination a step of bringing synthetic mica powder into contact with an aqueous solution composed of one or more of acid or chelating agent and a step of applying heat treatment to the synthetic mica at 600°–1350° C., the seventh invention concerns cosmetics, in which the synthetic mica of the first invention as described above is blended, the eighth invention concerns cosmetics, in which the synthetic mica of the second invention is blended and the ninth invention concerns cosmetics, in which the synthetic mica of the third invention is blended.

In the following, the present invention will be described more specifically.

The feature of the synthetic mica powder according to the first invention resides in that the mol number of fluorine in the synthetic mica is from 75 to 99% based on 2 mol of the synthetic mica as the stoichiometrical composition. If the mol number of fluorine (F) is less than 75% of the stoichiometrical composition, it is not desirable since the synthetic mica is decomposed and converted into forsterite ($MgSiO_4$), leucite ($KAlSi_2O_6$), etc. On the other hand, if the mol number of F exceeds 99%, it is not desirable as well since there is no recognizable difference with respect to the properties from those of the case of 2 mol composition. The mol number of F is from 75 to 99%, preferably, from 80 to 97.5% and, more preferably, from 90 to 95% of the stoichiometrical composition.

The general formula of the synthetic mica powder of the first invention is shown below:

$$X_{1\sim1}Y_{2\sim3}(Z_4O_{10})F_{1.5\sim1.99}$$

wherein X represents one or more of ions selected from the group consisting of $Na^+$, $K^+$, $Li^+$, $Ca^{2+}$, $Rb^{2+}$, $Sr^{2+}$, Y represents one ore more of ions selected from the group consisting of $Mg^{2+}$, $Fe^{2+}$, $Ni^{2+}$, $Mn^{2+}$, $Al^{3+}$, $Fe^{3+}$ and $Li^+$, and Z represents one or more of ions selected from the group consisting of $Al^{3+}$, $Si^{4+}$, $Ge^{4+}$, $Fe^{3+}$ and $B^{3+}$.

The production process for the synthetic mica powder according to the first invention resides in applying heat treatment at 600° to 1350° C. to the synthetic mica. If the temperature is lower than 600° C., it is not preferred since the mol number of fluorine can not be decreased. While on the other hand, if the temperature exceeds 1350° C., it is not preferred since the synthetic mica is melted. The temperature for the heat treatment ranges from 600° to 1350° C., preferably 700° to 1200° C., and more preferably 900° to 1100° C.

The time for the heat treatment can optionally be selected depending on the processing temperature from several seconds to several days and a processing time of about from 0.5 to 10 hours is preferred in the case of treating the synthetic fluoro-phlogopite, for example, at a temperature of 1000° C.

As the general process for producing synthetic mica, for example, in the case of synthetic fluoro-phlogopite, about 40 parts of anhydrous silicic acid, about 30 parts of magnesium oxide, about 13 parts of aluminum oxide and about 17 parts of potassium silicofluoride are mixed and then melted at 1400°–1500° C., and then crystallized at 1300°–1400° C. to obtain synthetic fluoro-phlogopite ($KMg_3(AlSi_3O_{10})F_2$). After preparing the synthetic mica in this way, the obtained ingots are pulverized and classified, if required, to obtain synthetic mica powder.

In the case of pulverizing ingots, generally, the coarse pulverization is at first conducted and then fine pulverization is applied. The heat treatment may be applied either after the coarse pulverization of ingots or after fine pulverization. In the present invention, heat treatment is preferably applied after the pulverization and classification since it is excellent in view of shortening the processing time and increasing the processing effect.

For the facility and the system of applying heat treatment to the synthetic mica, all of known means can be used, for example, an external heating type heating furnace, an internal heating type heating furnace, a rotary kiln, etc.

The atmosphere for the heat treatment may be oxidizing atmosphere, reducing atmosphere, argon gas atmosphere, $N_2$ atmosphere, ammonia atmosphere, vacuum, etc. or the combination of them, which may be appropriately selected depending on the application use and the function. The particle size of the synthetic mica powder with less mol number of F according to the present invention, while varying depending on the application use, is generally from 0.05 to 2 μm along the thickness and from 2 to 60 μm along the plane.

The amount of the synthetic mica powder blended with the cosmetics is from 1 to 100% by weight based on the total amount of the cosmetics.

The end face of the particle of the synthetic mica powder according to the second invention has to be laminar. If it is not laminar, synthetic mica powder capable of attaining the purpose according to the present invention can not be obtained. Conventional synthetic mica powder has been prepared generally from laminar crystallized product of from several millimeters to several centimeters obtained by the melt-synthesis process by coarsely pulverizing in a dry pulverizer, for example, a jaw crusher or a hammer crusher and, thereafter, further pulverizing in a fine pulverizer. The shape of the thus obtained synthetic mica powder is an indefinable plate-like shape and the shape at the end face of the particle is planar and no lamination at the end face can be recognized. Lamination at the end face of the particle means such a state in which the shape at the end face of the particle is cleaved into at least two leaves. It is sufficient that the number of cleavage at the end face is two or more and it is more preferred as the number of cleavage is increased. Accordingly, the conventional synthetic mica powder in which the end face of the particle does not cleave into two or more leaves but is in a plane shape does not belong to the powder of synthetic mica according to the present invention. The end face of the particle means the face along the thickness (not along the plane) of the respective synthetic mica powder after powderization.

The particle size of the synthetic mica powder in which the end face is laminated according to the second invention, while varying depending on the application use, generally ranges from 0.05 to 2 μm along the thickness and from 2 to 60 μm along the plane.

The apparent thickness of the synthetic mica according to the present invention appears to be increased in view of the voids as compared with the conventional synthetic mica powder. However, since the end face of the particle is laminated and cleaved, the specific surface area of the particle is increased.

The synthetic mica according to the second invention is represented by the following general formula: $X_{1\sim 1}Y_{2\sim 3}(Z_4O_{10})F_2$, in which X represents one or more of ions selected from the group consisting of $Na^+$, $K^+$, $Li^+$, $Ca^{2+}$, $Rb^{2+}$ and $Sr^{2+}$, Y represents one or more of ions selected from the group consisting of $Mg^{2+}$, $Fe^{2+}$, $Ni^{2+}$, $Mn^{2+}$, $Al^{3+}$, $Fe^{3+}$ and $Li^+$ and Z represents one or more of ions selected from the group consisting of $Al^{3+}$, $Si^{4+}$, $Ge^{4+}$, $Fe^{3+}$ and $B^{3+}$.

The feature of the production process for the synthetic mica powder according to the second invention resides in bringing the synthetic mica powder into contact with an aqueous solution comprising one or more of acid or chelating agent.

As the general production process for the synthetic mica powder, synthetic fluoro-phlogopite ($KMg_3(AlSi_3O_{10})F_2$), for instance, is obtained in the same manner as the first invention. The synthetic fluoro-phlogopite ingots thus obtained are pulverized and, if required, classified to obtain synthetic fluoro-phlogopite powder.

The synthetic fluoro-phlogopite powder obtained in the above-mentioned example is in the indefinable plate-like shape and the shape at the end face of the particle is flat.

The synthetic mica powder having the shape in which the end face of the particle is laminated according to the second invention is obtained by bringing the synthetic mica powder obtained in the general production process as described above into contact with an aqueous solution comprising one or more of acid or chelating agent. For instance, there can be mentioned a production process of bringing the synthetic fluoro-phlogopite powder into contact with an aqueous solution of citric acid.

The time of contact with the aqueous solution is from several minutes to several days, which can be properly selected depending on the processing temperature and the processing concentration. In the case of bringing the fluoro-phlogopite into contact with 1M/l citric acid solution at 20° C., for example, from 30 minutes to 5 hours of time is preferred.

In the case of pulverizing ingots, coarse pulverization and fine pulverization are generally applied in this order, but contact with the aqueous solution may be conducted either after the coarse pulverization or after the fine pulverization. Contact after the fine pulverization and classification is excellent in view of the effect.

The contact temperature can be selected properly from 0° to 100° C., and higher temperature is preferred since the lamination can be promoted.

The concentration of the aqueous solution for the contact can properly be selected depending on the amount of the synthetic mica powder and it is generally from 0.05 to 10M/l.

As the method of bringing the synthetic mica powder into contact with the aqueous solution, any of known methods may be applied, for example, stirring by an agitator, aeration dipping, etc.

As the acid, either of inorganic or organic acid may be used and weak acid is preferably used since the structure may possibly be destroyed in the case of using a strong acid. The inorganic acid can include, for example, hydrochloric acid, nitric acid, sulfuric acid, chloric acid, perchloric acid, periodic acid, bromic acid, phosphoric acid, boric acid and carbonic acid. The organic acid can include, for example, carboxylic acid such as, formic acid, acetic acid, acrylic acid, benzoic acid, oxalic acid, malonic acid, succinic acid, glutaric acid, adipic acid, pimelic acid and phthalic acid, oxycarboxylic acid such as, lactic acid, maleic acid, tartaric acid and citric acid, amino acid such as glycine, alanine, valine, leucine, tyrosine, thoreonine, serine, proline, triptophane, methionine, cystine, thyroxine, asparagine, glutamic acid, lysine and alginine. The chelating agent can include, for example, ethylenediamine tetraacetic acid, nitrotriacetic acid, 1,2-diaminocyclohexane-tetraacetic acid, N-oxyethylene ethylenediaminetriacetic acid, ethyleneglycolbis-tetraacetic acid, ethylenediamine tetrapropionic acid, etc.

The amount of the synthetic mica powder blended with the cosmetics is from 1 to 100% by weight based on the total amount of the cosmetics.

The feature of the synthetic mica powder according to the third invention is that the mol number of fluorine (F) in the synthetic mica is from 75 to 99% to 2 mol of the synthetic mica as the stoichiometrical composition. If the mol number of F is less than 75% of the stoichiometrical composition, it is not preferred since the synthetic mica is decomposed into forsterite ($MgSiO_4$), leucite ($KAlSi_2O_6$), etc. On the other hand, if the mol number of F exceeds 99%, it is not desirable since there is no particular difference in the properties with respect to those of the 2 mol composition. The mol number of F is from 75 to 99%, preferably, from 80 to 97.5% and, more preferably, from 90 to 95% of the stoichiometrical composition.

The general formula of the synthetic mica powder of the third invention shown below:

$$X_{1\sim 1}Y_{2\sim 3}(Z_4O_{10})F_{1.5\sim 1.99}$$

wherein X represents one or more of ions selected from the group consisting of $Na^+$, $K^+$, $Li^+$, $Ca^{2+}$, $Rb^{2+}$, $Sr^{2+}$, Y represents one or more of ions selected from the group consisting of $Mg^{2+}$, $Fe^{2+}$, $Ni^{2+}$, $Mn^{2+}$, $Al^{3+}$, $Fe^{3+}$ and $Li^+$, and Z represents one or more of ions selected from the group consisting of $Al^{3+}$, $Si^{4+}$, $Ge^{4+}$, $Fe^{3+}$ and $B^{3+}$.

The end face of the particle of the synthetic mica powder according to the third invention has to be laminar. If it is not laminar, the synthetic mica capable of obtaining the purpose of the third invention can not be obtained. Conventional synthetic mica powder is generally obtained from laminar crystal products of several millimeters to several centimeters size obtained formed by the melt-synthesis method by coarsely pulverizing in a dry pulverizer, for example, a jaw crusher or a hammer crusher and then further pulverizing or grinding in a fine pulverizer. The shape of the thus obtained synthetic mica powder is an indefinable plate-like in which no lamination is found at the end face of the particle. Lamination at the end face of the particle means such a state in which the end face of the particle is cleaved into at least two leaves. It is sufficient that the number of cleveage at the end face is at least two or more and it is more desirable that the number of cleavage is increased. Accordingly, the synthetic mica powder in which the end face of the particle is not cleaved into two or more of leaves and merely takes a planar shape does not belong to the synthetic mica powder according to the present invention. The end face of the particle means the face along the respective thickness (not along the plane) of the respective synthetic mica powder after powderization.

The particle size of the synthetic mica according to the third invention, while varying depending on the application use, is generally from 0.05 to 2 μm along the thickness and from 2 to 60 μm along the direction of the plane.

The apparent thickness of the synthetic mica powder according to the third invention appears to be greater due to voids as compared with the conventional synthetic mica powder. However, since the end face of the particle is laminated and cleaved, the specific surface area of the particle is increased.

Explanation will then be made to the process for producing synthetic mica according to the third invention. At first, explanation will be made to the step of reducing the mol number of fluorine in the synthetic mica to 75-99% for 2 mol of the conventional stoichiometrical composition.

As the general production process for the synthetic mica, synthetic fluoro-phlogopite ($KMg_3(AlSi_3O_{10})F_2$) is obtained by mixing about 40 parts of anhydrous silicic acid, about 30 parts of magnesium oxide, about 13 parts of aluminum oxide and about 17 parts of potassium silicofluoride, which are then melted at 1400°–1500° C. and crystallized at 1300°–1400° C. After obtaining the synthetic mica in this way, the thus obtained ignots are pulverized and, if required, classified to obtain synthetic mica powder.

Synthetic mica with reduced mol number according to the present invention can be obtained by subjecting the conventional synthetic powder to heat treatment at 600°–1350° C. If the temperature is less than 600° C., it is not preferable since the mol number of fluorine can not be reduced. While on the other hand, if the temperature exceeds 1350° C., it is not preferable since the synthetic mica is malted. The heat treating temperature is within a range from 600° to 1350° C., preferably from 700° to 1200° C. and, more preferably 900° to 1100° C.

The time for heat treatment can properly be selected from several seconds to several days depending on the processing temperature and a processing time from about 0.5 to 10 hours is preferred in the case of processing the synthetic fluoro-phlogopite at 1000° C., for instance.

The heat treatment may be applied either after the coarse pulverization or after the fine pulverization of the ingots of synthetic mica. Heat treatment is preferably applied after the fine pulverization and classification, since it is excellent in view of shortening the processing time and improving the effect. For the system and facility of applying heat treatment to the synthetic mica, all of known methods can be applied such as an external heating type heating furnace, an internal heating type heating furnace, a rotary kiln, etc. The atmosphere for the heat treatment may be oxidizing atmosphere, reducing atmosphere, argon gas atmosphere, $N_2$ gas atmosphere, ammonia gas atmosphere, vacuum and combination thereof, which can selected properly depending on the application use and function.

Explanation will be made to the lamination at the end face of the particle in the synthetic mica powder.

For example, the shape of the synthetic fluoro-phlogopite powder is indefinable plate-like and the shape of the end face of the particle is flat. For making the end face of the particles laminar, the synthetic mica powder is brought into contact with an aqueous solution comprising one or more of acid or chelating agent. For instance, there can be mentioned a method of bringing the synthetic fluoro-phlogopite powder in contact with an aqueous solution of citric acid.

The time of contact with the aqueous solution is from several minutes to several days, which can be properly selected depending on the processing temperature and the processing concentration and it is, preferably, about from 30 min to 5 hours in the case, for example, of bringing the synthetic fluoro-phlogopite into contact with a solution of 1M/l citric acid at 20° C.

The pulverization for the ingots is generally carried out by the coarse pulverization and then fine pulverization in this order. Contact with the aqueous solution may be conducted either after the coarse pulverization or after the fine pulverization of the synthetic mica ingots. Contact after the pulverization and classification is excellent in view of the effect.

The temperature for contact can be selected properly from 0° to 100° C. and higher temperature is more preferred since it can promote the lamination.

The concentration of the aqueous solution for contact can properly be selected depending on the amount of the synthetic mica and it is generally from 0.05 to 10M/l.

As the method of bringing the synthetic mica powder into contact with the aqueous solution, any of known methods can be applied, for example, agitation by a stirrer and aeration dipping, etc.

As the acid and the chelating agent, those inorganic and organic acids, as well as chelating agents exemplified for the second invention can be used.

The synthetic mica in which the mol number of F is reduced and the end face of the particle is laminated according to the third invention can be obtained by applying the two steps described above successively. That is, the method comprises a step of bringing the synthetic mica powder into contact with an aqueous solution comprising one or more of acid or chelating agent and a step of applying heat treatment at 600°–1350° C. to the synthetic mica powder. The order for conducting the steps is optional and can properly be selected.

The amount of the synthetic mica powder blended to the cosmetics is from 1 to 100% by weight based on the total amount of the cosmetics.

The cosmetics concerning the present invention include those versatile cosmetics, such as facial cosmetics, make-up cosmetics and hair cosmetics. The present invention is particularly suitable to make-up cosmetics, for example, foundation, face powder, eye shadow, brusher, cosmetic bases, nail enamel, eye liner, mass color, lip sticks and fancy powder.

The synthetic mica powder according to the present invention may be blended with the cosmetics after applying treatment, if required, with silicone, metal soap, fatty acid, surface active agent, acid, alkali or inorganic salt, or combination thereof.

The addition to the synthetic mica powder, other ingredients used ordinarily for the cosmetics can properly be blended to the cosmetics in the present invention. They can include, for example, inorganic powder such as talc, kaolin, sericite, natural mica, phlogopite, lepidolite, biotite, lithia mica, vermiculite, magnesium carbonate, calcium carbonate, diatomaceous earth, magnesium silicate, calcium silicate, aluminum silicate, barium silicate, barium sulfate, strontium silicate, metal tungstate, silica, hydroxyapatite, zeolite, boron nitrate, and ceramics powder; organic powder such as nylon powder, polyethylene powder, polystyrene powder, benzoguanamine powder, polytetrafluoro-ethylene powder, distryrene benzene polymer powder, epoxy powder, acryl powder and finely crystalline cellulose; inorganic white pigment such as titanium oxide and zinc oxide, inorganic red pigment such as iron oxide (red iron oxide) and iron titanate, inorganic brown pigment such as γ-iron oxide; inorganic yellow pigment such as yellow iron oxide, loess, etc., inorganic black pigment such as black iron oxide and carbon black, inorganic purple pigment such as Mango Violet and cobalt violet; inorganic green pigment such as chromium oxide, chromium hydroxide and cobalt titanate; inorganic blue pigment such as ultramarine and prussian blue; pearl pigment such as titanium oxide-coated mica, titanium oxide-coated bismuth oxychloride, bismuth oxychloride, titanium oxide-coated talc, fish scale foil, and blue titanium oxide-coated mica; metal powder such as aluminum powder and copper powder; organic pigment such as red # 201, red # 202, red # 204, red # 205, red # 220, red # 226, red # 228, red # 405, orange # 203, orange # 204, yellow # 205, yellow # 401 and blue # 404. Organic pigment of zirconium, barium or aluminum lake such as red # 3, red # 104, red # 106, red # 227, red # 230, red # 401, red # 505, orange # 205, yellow # 4, yellow # 5, yellow # 202, yellow # 203, green # 3 and blue # 1; natural dye such as chlorophyll and β-carotene; various kinds of hydrocarbons such as squalane, liquid paraffin, vaseline, microcrystalline wax, ozocerite, ceresine, myristic acid, palmitic acid, stearic acid, oleic acid, isostearic acid, cetyl alcohol, hexadecyl alcohol, oleyl alcohol, cetyl-2-ethyl hexanoate, 2-ethyl-hexyl palmitate, 2-octyldodecyl myristate, neopentyl glycol di-2-ethyl hexanoate, glycerol tri-2-ethyl hexanoate, 2-octyldodecyl oleate, isopropyl myristate, glycerol triisostearate, glycerol tricoconut oil fatty acid, glycerol tri-2-ethyl hexanoate, 2-octyldodecyl oleate, isopropyl myristate, glycerol triisostearate, glycerol tricoconut oil fatty acid, olive oil, avocado oil, bees wax, myristyl myristate, mink oil and lanoline; oil ingredients such as silicone oil, higher fatty acid, oil and fat esters, higher alcohols and waxes; organic solvents such as acetone, toluene, butyl acetate and acetic acid ester; resins such as alkyl resin and urea resin, plasticizers such as camphor and acetyltributyl citrate; UV absorber, antioxidant, corrosion inhibitor, surface active agent, humectant, perfume, water, alcohol and viscosity improver.

The cosmetics according to the present invention may be in any of forms such as powder, cake, pencil, stick, patch, liquid, emulsion or cream.

The cosmetics according to the present invention may be in any of forms such as powder, cake, pencil, stick, ointment, liquid, emulsion or cream.

BRIEF EXPLANATION FOR DRAWING

BEST MODE FOR CARRYING OUT THE INVENTION

Figure 1:
FIG. 1 is an electron microscopic photograph ($\times 5000$) illustrating the surface state of synthetic mica powder in which the end face is laminated obtained in Preparation Example 5 according to the present invention.
Figure 2:
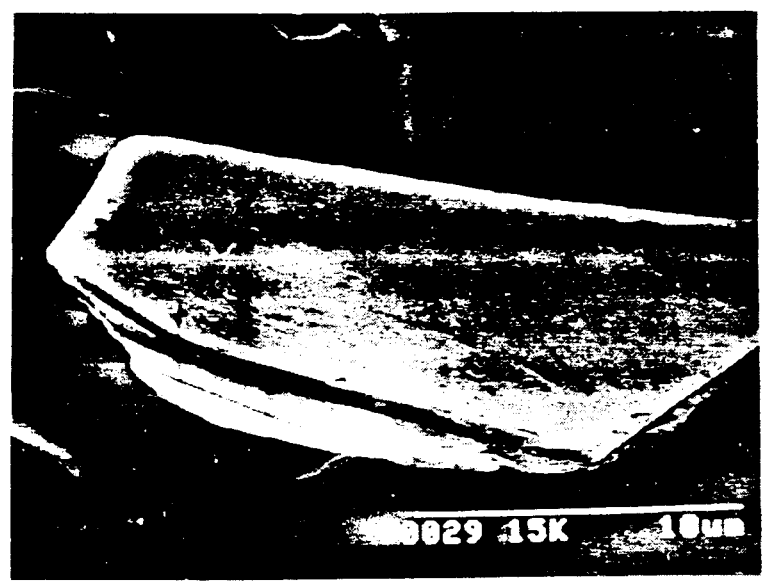
FIG. 2 is an electron microscopic photograph ($\times 5000$) illustrating the surface state of synthetic mica powder obtained in comparative Preparation Example 5.
Figure 3:
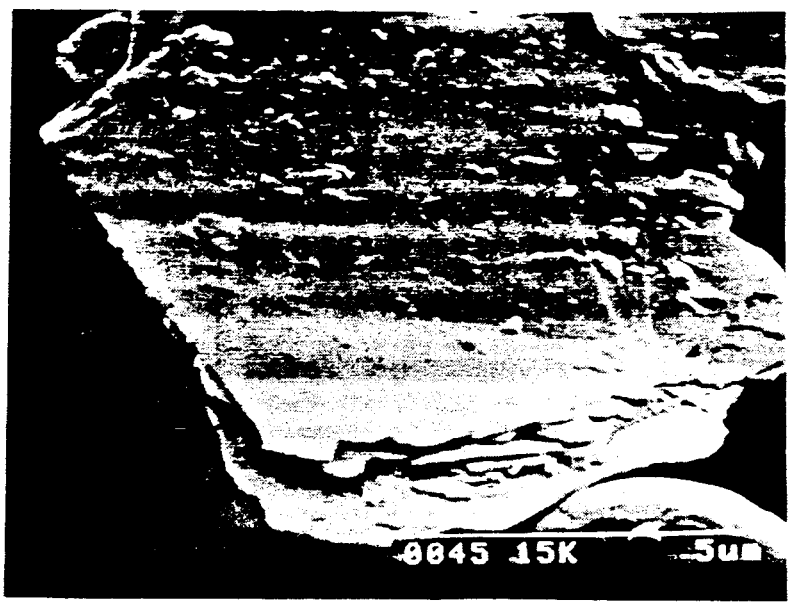
FIG. 3 is an electron microscopic photograph ($\times 10000$) illustrating the surface state of synthetic mica powder with less mol number of fluorine in which the end face is laminated obtained in Preparation Example 10 according to the present invention.
Figure 4:
FIG. 4 is an electron microscopic photograph ($\times 5000$) illustrating the surface state of synthetic mica powder obtained in Comparative Preparation Example 11 according to the present invention.

The present invention is further explained next referring to preparation examples, comparative preparation examples and examples but the invention is not limited to these examples. At first, the preparation example for the synthetic mica according to the present invention is explained. The chemical analysis value and the result of the measurement for the X-ray diffraction in the preparation examples are obtained by the method described below.

Chemical Analysis Value

Analysis was conducted by flame photometry for potassium, magnesium, atomic absorption photometry for aluminum, weight method for silica and absorptiometry for fluorine.

X-ray Diffraction

A measuring chart by broad angle X-ray diffractiometry for $2\theta = 2°-50°$ is shown. The measurement was conducted at 30 KV, 25 mA using slit system: D.S.=1°, S.S.=1°, R.S.=0.22 mm. The measuring conditions were 25° C. and 65% RH.

Fluorine Leaching Amount

F concentration of the liquid filtrate obtained from specimen 20 g/200 ml distilled water after stirring for 30 min. under the ambient temperature. Fluorine was analyzed by absorptiometry.

Potassium Leaching Amount

K concentration of the liquid filtrate obtained from specimen 20 g/200 ml distilled water after stirring for 30 min. under the ambient temperature. Potassium was analyzed by flame photometry.

Surface Activity

To a viorex glass tube of 4 mm inner diameter, 20 mg of powder was secured by quartz wool, through which t-butanol was passed at 250° C. and the decomposing rate was measured.

t-Butanol charging amount: 0.3 μl
Carrier gas: nitrogen
Flow rate: 50 ml/min

Analysis was conducted by using GV-7A manufactured by Shimazu Corp. with column PEG-20M, 0.31 mm×25 m and at column temperature at 80° C. The evaluation for the surface activity was shown by the residual rate of t-butanol.

Color

Powder was charged into a powder measuring cell made of quartz glass, measured by a Hitachi color analyzer 607 and H.V.C. values were calculated based on values X,Y,Z and the whiteness was shown by the V value.

PREPARATION EXAMPLE 1

After mixing 40 parts of anhydrous silicic acid, 30 parts of magnesium oxide, 13 parts of aluminum oxide and 17 parts of potassium silicofluoride, the resulting mixture was melted at 1500° C. The, synthetic fluorine mica crystallized at 1350° C. was pulverized and classified to obtain 100 parts of synthetic fluoro-phlogopite of 2.5 μm particle size (the sphere conversion value measured by Sedigraph 5000-01 type manufactured by Micromeritics Co.: here and hereinafter).

The powder was applied with heat treatment at 1100° C. for one hour in an Erema type electric furnace to obtain synthetic mica powder (2.6 μm grain size) of the present invention.

PREPARATION EXAMPLE 2

After mixing 50 parts of anhydrous silicic acid, 20 parts of magnesium oxide, 10 parts of lithium carbonate and 22 parts of sodium silicofluoride, the resulting mixture was melted at 1500° C. Then, sodium taeniolite crystallized at 1350° C. was pulverized and classified to obtain 100 parts of sodium taenilite of 6.0 μm particle size.

The powder was applied with heat treatment at 700° C. for one hour in an Erema type electric furnace to obtain synthetic mica powder (6.0 μm grain size) of the present invention.

PREPARATION EXAMPLE 3

After mixing 40 parts of anhydrous silicic acid, 30 parts of magnesium oxide, 13 parts of aluminum oxide and 17 parts of potassium silicofluoride, the resulting mixture was melted at 1500° C. The, synthetic fluorine mica crystallized at 1350° C. was pulverized and classified to obtain 100 parts of synthetic fluoro-phlogopite of 2.5 μm particle size.

The powder was applied with heat treatment at 1300° C. for 10 min. in an Erema type electric furnace to obtain synthetic mica powder (2.6 μm grain size) of the present invention.

COMPARATIVE PREPARATION EXAMPLE 1

Synthetic fluoro-phlogopite was synthesized by melting in the same manner as in Preparation Example 1, pulverized and classified and then applied with heat treatment in an Erema type electric furnace at 500° C. for 8 hours in the same manner as in Example 1 to obtain synthetic mica powder.

COMPARATIVE PREPARATION EXAMPLE 2

Synthetic sodium taeniolite was synthesized by melting in the same manner as in Preparation Example 2, pulverized and classified and then applied with heat treatment in an Erema type electric furnace at 500° C. for 8 hours in the same manner as in Example 1 to obtain synthetic mica powder.

PREPARATION EXAMPLE 4

After mixing 40 parts of anhydrous silicic acid, 30 parts of magnesium oxide, 13 parts of aluminum oxide and 17 parts of potassium silicofluoride, the resulting mixture was melted at 1500° C. Then, synthetic fluorine mica crystallized at 1350° C. was pulverized and classified to obtain 100 parts of synthetic fluoro-phlogopite of 2.5 μm particle size.

The powder was applied with heat treatment at 900° C. for 8 hours in an Erema type electric furnace to obtain synthetic mica powder (2.6 μm grain size) of the present invention.

COMPARATIVE PREPARATION EXAMPLE 3

Synthetic fluoro-phlogopite was synthesized by melting in the same manner as in Preparation Example 1, pulverized and classified and then applied with heat treatment in an Erema type electric furnace at 1400° C. for one hour in the same manner as in Example 1 to obtain synthetic mica powder.

COMPARATIVE PREPARATION EXAMPLE 4

Synthetic sodium taeniolite was synthesized by melting in the same manner as in Preparation Example 2, pulverized and classified and then applied with heat treatment in an Erema type electric furnace at 1400° C. for one hour in the same manner as in Example 1 to obtain synthetic mica powder.

TABLE 1

|  | Preparation Example 1 | Preparation Example 2 | Preparation Example 3 | Preparation Example 4 |
|---|---|---|---|---|
| F mol (powder F mol/ stoichiometrical F mol) × 100 | 95 | 90 | 95 | 90 |
| F leaching amount (ppm) | less than 1 | less than 1 | less than 1 | less than 1 |
| K leaching amount (ppm) (Na) | less than 1 | less than 1 | less than 1 | less than 1 |
| Surface active agent ** | 100 | 98 | 100 | 98 |
| Whiteness (V value) | 9.1 | 8.9 | 9.1 | 9.0 |

|  | Comparative Preparation Example 1 | Comparative Preparation Example 2 | Comparative Preparation Example 3 | Comparative Preparation Example 4 |
|---|---|---|---|---|
| F mol (powder F mol/ stoichiometrical amount) × 100 | 100 | 100 | 70 | 65 |
| F leaching amount (ppm) | 20 | 42 | less than 1 | less than 1 |
| K leaching amount (ppm) (Na) | 8.7 | 21 | less than 1 | less than 1 |
| Surface active agent * | 52 | 61 | — ** | — |

TABLE 1-continued

| Whiteness (V value) | 7.9 | 5.6 | — | — |
|---|---|---|---|---|

* t-butanol residual rate.
** Measurement was impossible in view of melting and solidification.

Then, examples of cosmetics blended with the synthetic mica powder are shown. The performance of cosmetics was functionally estimated by five stages by 20 expert panelers for the items referred to in the following table.

TABLE 2

| Estimation | Estimated Item | | | | |
|---|---|---|---|---|---|
| | Extensibility | Adherence | Gloss | Smooth feeling in use | Smoothness of made-up skin |
| 1 | extremely poor | extremely poor | none | not smooth at all | extremely dirty |
| 2 | poor | poor | less | not smooth | dirty |
| 3 | ordinary | ordinary | ordinary | ordinary | ordinary |
| 4 | good | good | glossy | smooth | good |
| 5 | excellent | excellent | excellent | extremely smooth | extremely fine |

The result of the estimation was shown based on average values for 20 personnels by the symbols shown below.

⊚ ... 4.5–5.0
○ ... 3.5–4.5
△ ... 2.5–3.5
× ... 1.5–2.5
×× ... 1.0–1.5

EXAMPLE 1

Powder Foundation

The powder foundation X according to the present invention was prepared by each of the following ingredients.

| | | (wt %) |
|---|---|---|
| 1 | Titanium oxide | 7 |
| 2 | Talc | 20 |
| 3 | Muscovite | 3 |
| 4 | Synthetic mica powder of Preparation Example 1 | 55 |
| 5 | Nylon powder | 2 |
| 6 | Red iron oxide | 0.5 |
| 7 | Yellow iron oxide | 1 |
| 8 | Black iron oxide | 0.1 |
| 9 | Silicon oil | 1 |
| 10 | 2-Ethylhexyl palmitate | 9 |
| 11 | Sorbitan sesquioleate | 1 |
| 12 | Preservative | 0.3 |
| 13 | Perfume | 0.1 |

The ingredients 1–8 were mixed in a Henschel mixer and the ingredients 9–13 melted and mixed under heating were admixed to the mixture, which was then pulverized in a 5 HP pulverizer (of Hosokawa Micron) and then molded under the pressure of 160 kg/cm² into a pan of 5.3 cm diameter to obtain a powder foundation X according to the present invention.

A powder foundation Y for comparison was prepared in the same procedures as above except for using the identical amount of sericite instead of the synthetic mica powder of the ingredient 4. The result for the functional estimation are shown in the following table.

TABLE 3

| Powder foundation | Estimation Item | | | | |
|---|---|---|---|---|---|
| | Extensibility | Adherence | Gloss | Smooth feeling in use | Fineness of made-up skin |
| X (Invention) | ⊚ | ⊚ | ○ | ○ | ⊚ |
| Y (Comparison) | ○ | ○ | △ | △ | ⊚ |

As apparent from the table, it can be seen that the powder foundation X according to the present invention has higher estimation. Further, since the hardness of the foundation X of the present invention was 26, and that of the foundation for comparison was 46, it can be seen that the foundation X according to the present invention shows better molding state.

EXAMPLE 2

Brusher

A brusher X according to the present invention was prepared from each of the following ingredients.

| | | (wt %) |
|---|---|---|
| (1) | Talc | 12.5 |
| (2) | Sericite | 8.1 |
| (3) | Muscovite | 5.0 |
| (4) | Synthetic mica powder of Preparation Example 1 | 62.5 |
| (5) | Red # 226 | 0.4 |
| (6) | Titanium mica | 3.0 |
| (7) | Squalane | 3.0 |
| (8) | Ethylhexyl palmitate | 5.0 |
| (9) | Preservative | 0.3 |
| (10) | Perfume | 0.2 |

The ingredients (1), (2), (3), (4) and (5) were mixed in Henschel mixer and the ingredients (7), (8), (9) and (10) melted and mixed under heating were blown to the mixture and further mixed. Then, the resulting mixture was pulverized in a 5 HP pulverizer (of Hosokawa Micron), mixed with addition of the ingredient (6) and then molded under the pressure of 120 kg/cm² into a pan of 4×6 cm to obtain a brusher X according to the present invention.

A brusher Y for comparison was prepared in the same procedures as above except for replacing 62.5% by weight of the synthetic mica powder of the ingredient (4) with 20% by weight of sericite and 42.5% by weight of muscovite. The result for the functional estimation are shown in the table below.

TABLE 4

| Brusher | Estimation Item | | | | |
|---|---|---|---|---|---|
| | Extensibility | Adherence | Gloss | Smooth feeling in use | Fineness of made-up skin |
| X (Invention) | ○ | ○ | ○ | ○ | ⊚ |
| Y (Comparison) | △ | △ | △ | △ | ○ |

As apparent from the table, it can be seen that the brusher X according to the present invention is excellent in any of the items for the functional estimation. Further, since the hardness of the brusher X according to the present invention was 29, and that for the brusher Y for comparison was 35, it can be seen that the brusher according to the present invention has better moldability.

Further as the result of measuring the outer looking color of the molding product by the Hitachi color analyzer 607, the chroma of the brusher according to the present invention was 11.8, while that for the brusher & for comparison was 10.9, and it can be seen that the brusher X according to the present invention has higher chroma and shows clear outer looking color.

EXAMPLE 3

Fancy Powder

A fancy powder X according to the present invention was prepared from each of the following ingredients.

|  | (wt %) |
|---|---|
| (1) Synthetic mica powder of Preparation Example 2 | 95 |
| (2) Talc | 4 |
| (3) Perfume | 1 |
| (4) Iron oxide pigment | proper amount |

After mixing the ingredients (1), (2) and (4), the ingredient (3) was admixed which were charged in a container to obtain a fancy powder X according to the present invention.

A fancy powder Y for comparison was prepared in the same procedures as above except for using the identical amount of talc instead of 95% by weight of the synthetic mica powder of the ingredient (1) (accordingly, 99% by weight in total). Perfume stability was compared in the functional estimation for the samples of each of the fancy powders X and Y preserved for one month in a thermostat at 37° C. and each of the control (just after the preparation of fancy powders X and Y prepared with the same formulations). In the case of the fancy powder X according to the present invention, there is no substantial change between the sample after one month preservation and the control. While on the other hand, in the case of the fancy powder Y for comparison, the odor of the sample after one month preservation was remarkably changed as compared with that of the control.

PREPARATION EXAMPLE 5

After mixing 40 parts of anhydrous silicic acid, 30 parts of magnesium oxide, 13 parts of aluminum oxide and 17 parts of potassium silicofluoride, the resulting mixture was melted at 1500° C. Then, synthetic fluorine mica crystallized at 1350° C. was coarsely pulverized and finely pulverized to obtain 100 parts of synthetic fluoro-phlogopite of 2.5 μm particle size (the sphere conversion value measured by Sedigraph 5000-01 type manufactured by Micromeritics Co.). 25 g of the powder was dispersed in 100 ml of an aqueous solution of citric acid (1M/l) and stirred by a table stirrer. The stirring was conducted at 80° C. for 60 min. Then, it was filtered in a Buchner funnel, washed and then dried to obtain synthetic mica powder (grain size 2.6 μm) of the present invention. When the powder was observed by scanning electron microscope, it was clear that the end face was burred and laminated. For the comparison, the not-treated synthetic mica powder was also observed in which the end face was flat and not laminated (Comparative Preparation Example 5).

PREPARATION EXAMPLE 6

After mixing 40 parts of anhydrous silicic acid, 30 parts of magnesium oxide, 13 parts of aluminum oxide and 17 parts of potassium silicofluoride, the resulting emulsion was melted at 1500° C. Then, synthetic fluorine mica crystallized at 1350° C. was coarsely pulverized and finely pulverized to obtain 100 parts of synthetic fluoro-phlogopite of 2.5 μm particle size (the sphere conversion value measured by Sedigraph 5000-01 type manufactured by Micromeritics Co.). 25 g of the powder was dispersed in 100 ml of water adjusted to pH 3 with diluted hydrochloric acid and stirred by a table stirrer. The stirring was conducted at 80° C. for 60 min., then, it was filtered, washed and then dried to obtain synthetic mica powder (grain size 2.6 μm) of the present invention. When the powder was observed by a scanning electron microscope, it was clear that the end face was burred and laminated.

PREPARATION EXAMPLE 7

After mixing 40 parts of anhydrous silicic acid, 30 parts of magnesium oxide, 13 parts of aluminum oxide and 17 parts of potassium silicofluoride, the resulting mixture was melted at 1500° C. Then, synthetic fluorine mica crystallized at 1350° C. was coarsely pulverized and ground to obtain 100 parts of synthetic fluoro-phlogopite of 2.0 μm particle size. 25 g of the powder was dispersed in 100 ml of an aqueous solution of maleic acid (1M/l) and stirred by a table stirrer. The stirring was conducted at 80° C. for 60 min. Then, it was filtered in a Buchner funnel, washed and then dried to obtain synthetic mica powder (grain size 2.1 μm) of the present invention. When the powder was observed by a scanning electron microscope, it was clear that the end face was burred and laminated. For the comparison, the not-treated synthetic mica powder was also observed in which the end face was flat and not laminated (Comparative Preparation Example 6).

PREPARATION EXAMPLE 8

After mixing 40 parts of anhydrous silicic acid, 30 parts of magnesium oxide, 13 parts of aluminum oxide and 17 parts of potassium silicofluoride, the resulting mixture was melted at 1500° C. Then, synthetic fluorine mica crystallized at 1350° C. was coarsely pulverized and ground to obtain 100 parts of synthetic fluoro-phlogopite of 8.5 μm grain size. 25 g of the powder was dispersed in 100m ml of an aqueous solution of 2-sodium ethylenediaminetetraacetate (1M/l) and stirred by a table stirrer. The stirring was conducted at 80° C. for 60 min. Then, it was filtered in a Buchner funnel, washed and then dried to obtain synthetic mica powder (grain size 8.6 μm) of the present invention. When the powder was observed by a scanning electron microscope, it was clear that the end face was burred and laminated. For the comparison, the not-treated synthetic mica powder was also observed in which the end face was flat and not laminated (Comparative Preparation Example 7).

PREPARATION EXAMPLE 9

After mixing 50 parts of anhydrous silicic acid, 20 parts of magnesium oxide, 10 parts of lithium carbonate and 22 parts of sodium silicofluoride, the resulting emulsion was melted at 1500° C. Then, synthetic fluorine mica crystallized at 1350° C. was coarsely pulverized and classified to obtain synthetic sodium taeniolite of 10 μm particle size. 25 g of the powder was dispersed in 100 ml of an aqueous solution of citric acid (1M/l) and stirred by a table stirrer. The stirring was conducted at 80° C. for 60 min. Then, it was filtered by a Buchner funnel, washed and then dried to obtain synthetic mica powder (grain size 10 μm) of the present invention. When the powder was observed by scanning electron microscope, it was clear that the end face was burred and laminated. For the comparison, the not-treated synthetic mica powder was also observed in which the end face was flat and not laminated (Comparative Preparation Example 8).

COMPARATIVE PREPARATION EXAMPLE 9

25 g of natural phlogopite powder (3.7 μm grain size) was dispersed into 100 ml of an aqueous solution of citric acid (1M/l) and stirred in a table stirrer. The stirring was carried out at a temperature 80° C. for 60 minutes. Then, it was filtered in a Buchner funnel, washed and then dried to obtain powder. When the powder was observed under a scanning electron microscope, the end face was flat and not laminated.

TEST EXAMPLE 1

A nail enamel composition was prepared by adding 5 parts of synthetic mica powder obtained in Preparation Examples 5-9 and Comparative Examples 5-9, 0.1 parts of titanium oxide and 0.3 parts of chromium oxide to 94.6 parts of a nail enamel clear base comprising 12 parts of nitrocelulose, 12 parts of modified alkyd resin, 5 parts of acetyl tributyl citrate, 1 part of organic-modified montmorillonite, 20 parts of toluene and 50 parts of ethyl acetate under stirring. The stability of the thus obtained nail enamel composition was estimated by the amount of precipitates after settling for one month.

o . . . not precipitated at all,
Δ. . . precipitated slightly.
x . . . precipitated

TABLE 5

|  | Stability |
| --- | --- |
| Preparation Example 5 | o |
| Comparative Preparation Example 5 | x |
| Preparation Example 6 | o |
| Preparation Example 7 | o |
| Comparative Preparation Example 6 | x |
| Preparation Example 8 | o |
| Comparative Preparation Example 7 | x |
| Preparation Example 9 | o |
| Comparative Preparation Example 8 | Δ |
| Comparative Preparation Example 9 | x |

Then, examples of cosmetics blended with the synthetic mica powder are shown.

The performance of the cosmetics are functionally estimated for five stages by 20 expert panelers regarding the items listed in the following table.

TABLE 6

| Estimation | Estimation Item | | | | | | |
| --- | --- | --- | --- | --- | --- | --- | --- |
|  | Extensibility | Adherence | Gloss | Adherence feeling | Fineness of madeup skin | Wear resistance | Fitness |
| 1 | extremely poor | extremely poor | none | none | extremely dirty | extremely peeling | extremely poor |
| 2 | poor | poor | less | less | dirty | peeling | poor |
| 3 | ordinary | ordinary | ordinary | ordinary | ordinary | ordinary | ordinary |
| 4 | good | good | present | present | fine | less peeling | good |
| 5 | excellent | excellent | extremely high | extremely high | extremely fine | much less peeling | excellent |

The result of the estimation is shown by the following symbols based on the average values obtained from 20 panellers.

⊚ . . . 4.5–5.0
o . . . 3.5–4.5
Δ. . . 2.5–3.5
x . . . 1.5–2.5
xx . . . 1.0–1.5

EXAMPLE 4

Powder Foundation

The powder foundation X according to the present invention was prepared by each of the following ingredients.

|  | | (wt %) |
| --- | --- | --- |
| 1 | Titanium oxide | 7 |
| 2 | Talc | 20 |
| 3 | Muscovite | 3 |
| 4 | Synthetic mica powder of Preparation Example 5 | 55 |
| 5 | Nylon powder | 2 |
| 6 | Red iron oxide | 0.5 |
| 7 | Yellow iron oxide | 1 |
| 8 | Black iron oxide | 0.1 |
| 9 | Silicon oil | 1 |
| 10 | 2-Ethylhexyl palmitate | 9 |
| 11 | Sorbitan sesquioleate | 1 |
| 12 | Preservative | 0.3 |
| 13 | Perfume | 0.1 |

The ingredients 1–8 were mixed in a Henschel mixer and then the ingredients 9–13 melted and mixed under heating were admixed to the mixture, which was then pulverized in a 5 HP pulverizer (of Hosokawa micron) and then molded under the pressure of 160 kg/cm² into a pan of 5.3 cm diameter to obtain a powder foundation X according to the present invention.

A powder foundation Y for comparison was prepared in the same procedures as above except for using the identical amount of sericite instead of the synthetic mica powder of the ingredient 4. The result for the functional estimation are shown in the following table.

TABLE 7

| Powder foundation | Estimation Item | | | | |
| --- | --- | --- | --- | --- | --- |
|  | Extensibility | Adherence | Gloss | Smooth feeling in use | Fineness of made-up skin |
| X (Invention) | o | o | o | ⊚ | ⊚ |
| Y (Comparison) | Δ | Δ | Δ | Δ | o |

As seen from the table, it can be seen that the powder foundation X according to the present invention has higher estimation. Further, it was, particularly, excellent in the adhering feeling. Further, since the hardness of the foundation X of the present invention was 22, and that of the foundation for comparison was 46, it can be seen that the foundation X according to the present invention shows better molding state.

EXAMPLE 5

Brusher

A brusher X according to the present invention was prepared from each of the following ingredients.

|  | (wt %) |
| --- | --- |
| (1) Talc | 12.6 |
| (2) Sericite | 8.1 |
| (3) Muscovite | 5.0 |
| (4) Synthetic mica powder of Preparation Example 6 | 62.5 |
| (5) Red # 226 | 0.4 |
| (6) Titanium mica | 3.0 |
| (7) Squalane | 3.0 |
| (8) 2-Ethylhexyl palmitate | 5.0 |
| (9) Preservative | 0.3 |
| (10) Perfume | 0.2 |

The ingredients (1), (2), (3), (4) and (5) were mixed in Henschel mixer and the ingredients (7), (8), (9) and (10) melted and mixed under heating were blown to the mixture and further mixed. Then, the resulting mixture was pulverized in a 5 HP pulverizer (of Hosokawa Micron), mixed with addition of the ingredient (6) and then molded under the pressure of 120 kg/cm² into a pan of 4×6 cm to obtain a brusher X according to the present invention.

A brusher Y for comparison was prepared in the same procedures as above except for replacing 62.5% by weight of the synthetic mica powder of the ingredient (4) with 20% by weight of sericite and 42.5% by weight of muscovite. The result for the functional estimation are shown in the table below.

TABLE 8

| Brusher | Estimation Item | | | | |
| --- | --- | --- | --- | --- | --- |
|  | Extensibility | Adherence | Gloss | Smooth feeling in use | Fineness of made-up skin |
| X (Invention) | ○ | ○ | ○ | ◉ | ○ |
| Y (Comparison) | △ | △ | △ | △ | ○ |

As apparent from the table, it can seen that the brusher X according to the present invention is excellent in any of the items for the functional estimation. Further, since the hardness of the brusher X according to the present invention was 27, whereas that for the brusher Y for comparison was 35, it can be seen that the brusher according to the present invention has better moldability.

Further, as the result of measuring the outer looking color of the molding product by the Hitachi color analyzer 607, since the chroma of the brusher according to the present invention was 11.5, while that for the brusher Y for comparison was 10.9, it can be seen that the brusher X according to the present invention has higher chroma and shows clear outer looking color.

EXAMPLE 6

Nail enamel

The nail enamel according to the present invention was prepared by each of the following ingredients.

|  | (wt %) |
| --- | --- |
| 1 Nitrocellulose | 12 |
| 2 Modified alkyd resin | 12 |
| 3 Acetyl tributyl citrate | 5 |
| 4 n-Butyl acetate | 36.4 |
| 5 Ethyl acetate | 6 |
| 6 n-Butyl alcohol | 2 |
| 7 Toluene | 21 |
| 8 Iron oxide pigment | 0.5 |
| 9 Titanium dioxide | 0.1 |
| 10 Pearl pigment | 2 |
| 11 Synthetic mica powder in Preparation Example 5 | 2 |
| 12 Organic-modified montmorillonite | 1 |

The ingredients 1–7 (the ingredient 4 was used partially) were dissolved and the ingredient 12 and the remaining portion of the ingredient 4 mixed into a gel-like state was admixed to the solution. Then, the ingredients 8–11 were further admixed and charged in a container to obtain the nail enamel according to the present invention.

A nail enamel Y for comparison was prepared by the same procedures as above except for using the same amount of sericite instead of the synthetic mica powder of the ingredient 11. The result of the functional estimation is shown in the following table.

TABLE 9

| Nail enamel | Estimation Item | |
| --- | --- | --- |
|  | Extensibility | Wear resistance |
| X (Invention) | ○ | ◉ |
| Y (Comparison) | △ | △ |

As apparent from the table, it can be seen that the nail enamel X according to the present invention is excellent in any of the items for the functional estimation. Particularly, the wear resistance was remarkable. Furthermore, since the synthetic mica powder is less precipitated as compared with sericite, it has a merit capable of decreasing the amount of the viscosity improver used.

EXAMPLE 7

Emulsion Foundation

The emulsion foundation X according to the present invention was prepared from each of the following ingredients.

|  | (wt %) |
| --- | --- |
| 1 Stearic acid | 0.4 |
| 2 Isostearic acid | 0.3 |
| 3 Cetyl 2-ethylhexanoate | 4 |
| 4 Liquid paraffin | 11 |
| 5 Polyxyethylene (10) stearyl ether | 2 |
| 6 Talc | 15 |
| 7 Pigment | 4 |
| 8 Cetyl alcohol | 0.3 |
| 9 Preservative | 0.09 |
| 10 Synthetic mica powder in Preparation Example 5 | 3 |
| 11 Triethanolamine | 0.42 |
| 12 Propylene glycol | 5 |
| 13 Ion exchanged water | 54.19 |
| 14 Perfume | 0.3 |

After over-heating at 85° C., dissolving and mixing the ingredients 1-9, the ingredient 10 was added and uniformly dispersed. Then, a mixture prepared by over-heating at 85° C., dissolving and mixing the ingredients 11-14 was gradually added thereto and emulsified. After maintaining the temperature upon emulsification for 10 min. and stirring, the resulting mixture was cooled to 45° C. while stirring. The ingredient 15 was added thereto and cooling under stirring was continued till 35° C. and the product was recovered and charged into a vessel to obtain an emulsion foundation X according to the present invention.

An emulsion foundation Y for comparison was prepared in the same manner as above except for using the same amount of talc instead of the synthetic mica powder of the ingredient 10. The results for the functional estimation are shown in the table below.

TABLE 10

| Emulsion foundation | Estimation Item | | | | | |
|---|---|---|---|---|---|---|
| | Extensibility | Adherence | Fitness | Gloss | Adherence feeling in use | Fineness on made-up skin |
| X (Invention) | ○ | ◉ | ○ | ◉ | ○ | ○ |
| Y (Comparison) | △ | △ | △ | △ | △ | △ |

As apparent from the table, the foundation X according to the present invention is excellent over the foundation Y for comparison. Further, foundation X according to the present invention was also excellent in aging stability (with no decomposition).

PREPARATION EXAMPLE 10

After mixing 40 parts of anhydrous silicic acid, 30 parts of magnesium oxide, 13 parts of aluminum oxide and 17 parts of potassium silicofluoride, the resulting mixture was melted at 1500° C. Then, synthetic fluorine mica crystallized at 1350° C. was coarsely pulverized and classified to obtain 100 parts of synthetic fluorophlogopite of 2.5 μm particle size (the sphere conversion value measured by Sedigraph 5000-01 type manufactured by Micromeritics Co.). 25 g of the powder was dispersed in 100 ml of an aqueous solution of citric acid (1 M/l) and stirred by a table stirrer. The stirring was conducted at 80°C. for 60 min. Then, it was filtered by Buchner funnel, washed and then dried, the powder was applied with heat treatment at 1100° C. for one hour in an Erema type electric furnace to obtain synthetic mica powder (particle size 2.5 μm) of the present invention. When the powder was observed by a scanning electron microscope, it was clear that the end face was burred and laminated. For the comparison, the synthetic mica powder without using the treatment of citric acid aqueous solution was observed, but the end face was flat and not laminated (Comparative Preparation Example 10).

COMPARATIVE PREPARATION EXAMPLE 11

Synthetic fluoro-phlogopite was melt-synthesized in the same manner as in Preparation Example 10, pulverized and classified in the same manner as Preparation Example 10 and then applied with heat treatment at 500° C. for 8 hours in an Erema type electric furnace to obtain synthetic mica powder.

PREPARATION EXAMPLE 11

After mixing 40 parts of anhydrous silicic acid, 30 parts of magnesium oxide, 13 parts of aluminum oxide and 17 parts of potassium silicofluoride, the resulting mixture was melted at 1500° C. Then, synthetic fluorine mica crystallized at 1350° C. was coarsely pulverized and classified to obtain synthetic fluoro-phlogopite of 3.5μ particle size. 25 g of the powder was dispersed in 100 ml of an aqueous solution of maleic acid (1 M/l) and stirred by a table stirrer. The stirring was conducted at 80° C. for 60 min. Then, it was filtered by a Buchner funnel, washed, dried and then applied with heat treatment at 100° C. for 4 hours in an Erema type electric furnace to obtain synthetic mica powder (particle size 3.5 μm) of the present invention. When the powder was observed by a scanning electron microscope, it was clear that the end face was burred and laminated. For the comparison, the synthetic mica powder not treated with maleic acdid was also observed in which the end face was flat and not laminated (Comparative Preparation Example 12).

PREPARATION EXAMPLE 12

After mixing 40 parts of anhydrous silicic acid, 30 parts of magnesium oxide, 13 parts of aluminum oxide and 17 parts of potassium silicofluoride, the resulting mixture was melted at 1500° C. Then, synthetic fluorine mica crystallized at 1350° C. was coarsely pulverized and classified to obtain 100 parts of synthetic fluorophlogopite of 8.0 μm grain size. 25 g of the powder was dispersed in 100 ml of an aqueous solution of disodium ethylenediaminetetraacetate (1 M/l) and stirred by a table stirrer. The stirring was conducted at 80° C. for 60 min. Then, it was filtered by Buchner funnel, washed, dried and then applied with heat treatment at 1000° C. for 4 hours in an Erema type electric furnace to obtain the synthetic mica powder (particle size 8.0 μm) of the present invention. When the powder was observed by a scanning electron microscope; it was clear that the end face was burred and laminated.

PREPARATION EXAMPLE 13

After mixing 50 parts of anhydrous silicic acid, 20 parts of magnesium oxide, 10 parts of lithium carbonate and 22 parts of sodium silicofluoride, the resulting mixture was melted at 1500° C. Then, synthetic fluorine mica crystallized at 1350° C. was coarsely pulverized and classified to obtain 100 parts of synthetic sodium taeniolite of 6.0 μm particle size. 25 g of the powder was dispersed in 100 ml of an aqueous solution of citric acid (1 M/l) and stirred by a table stirrer. The stirring was conducted at 80° C. for 60 min. Then, it was filtered by a Buchner funnel, washed, dried and then applied with heat treatment at 700° C. for 2 hours to obtain synthetic mica powder (particle size 6.0 μm) of the present invention. When the powder was observed by a scanning electron microscope, it was clear that the end face was burred and laminated. For the comparison, the synthetic mica powder without applying treatment with aqueous solution of citric acid was observed to find that the end face was flat and not laminated (Comparative Preparation Example 13).

PREPARATION EXAMPLE 14

After mixing 40 parts of anhydrous silicic acid, 30 parts of magnesium oxide, 13 parts of aluminum oxide and 17 parts of potassium silicofluoride, the resulting mixture was melted at 1500° C. Then, synthetic fluorine mica crystallized at 1350° C. was coarsely pulverized and classified to obtain 100 parts of synthetic fluorophlogopite of 2.5 μm particle size (the sphere conversion value measured by Sedigraph 5000-01 type manufactured by Micromeritics Co.). 25 g of the powder was dispersed in 100 ml of water adjusted to pH 3 with diluted hydrochloric acid and stirred by a table stirrer. The stirring was conducted at 80° C. for 60 min. Then, it was filtered by Buchner funnel, washed, dried and then applied with heat treatment at 1100° C. for one hour in an Erema type electric furnace to obtain the synthetic mica powder (particle size 2.5 μm) of the present invention. When the powder was observed by a scanning electron microscope, it was clear that the end face was burred and laminated.

COMPARATIVE PREPARATION EXAMPLE 14

Synthetic sodium taeniolite was melt-synthesized in the same procedures as in Preparation Example 11, pulverized and classified in the same manner as in Preparation Example 2 to obtain synthetic sodium taeniolite powder. The powder was applied with heat treatment at 500° C. for 8 hours in an Erema type electric furnace to obtain the synthetic mica powder.

COMPARATIVE PREPARATION EXAMPLE 15

Synthetic mica powder was obtained by the same procedures as in Comparative Preparation Example 11 except for bringing (25 g of powder) into contact with 100 ml of an aqueous solution of citric acid (1 M/l) before heat treatment.

TEST EXAMPLE 2

A nail enamel composition was prepared by adding 5 parts of synthetic mica powder obtained in Preparation Examples 10–14 and Comparative Examples 10–15, 0.1 parts of titanium oxide and 0.3 parts of chromium oxide to 94.6 parts of a nail enamel clear base comprising 12 parts of nitrocellulose, 12 parts of modified alkyd resin, 5 parts of acetyl tributyl citrate, 1 parts of organic-modified montmorillonite, 20 parts of toluene and 50 parts of ethyl acetate under stirring. The stability of the thus obtained nail enamel composition was estimated by the amount of precipitates after leaving for one month.

○ ... not precipitated at all,
Δ ... precipitated slightly.
x ... precipitated

TABLE 11

|  | Preparation Example 10 | Preparation Example 11 | Preparation Example 12 | Preparation Example 13 | Preparation Example 14 | Comparative Preparation Example 10 |
|---|---|---|---|---|---|---|
| Kind of mica | Fluorophlogopite | Fluorophlogopite | Fluorophlogopite | Sodium taeniolite | Fluorophlogopite | Fluorophlogopite |
| Aqueous solution for contact | citric acid | citric acid | EDTA | citric acid | hydrochloric acid | — |
| Heat treatment temperature (°C.) | 1100 | 1000 | 1000 | 700 | 1100 | 1100 |
| End face shape | laminated | laminated | laminated | laminated | laminated | flat |
| F mol % (%) (powder F mol number/stoichiometrical F mol number × 100) | 95 | 95 | 95 | 95 | 95 | 95 |
| F leaching amount (ppm) | less than 1 | less than 1 | less than 1 | less than 1 | less than 1 | less than 1 |
| K leaching amount (ppm) | less than 1 | less than 1 | less than 1 | less than 1 | less than 1 | less than 1 |
| Surface activity (t-butanol residue %) | 100 | 97 | 98 | 100 | 96 | 98 |
| Whiteness (V value) | 9.1 | 9.0 | 8.9 | 9.0 | 8.9 | 8.8 |
| Stability | ○ | ○ | ○ | ○ | ○ | X |
| Overall estimation | ⦿ | ⦿ | ⦿ | ⦿ | ⦿ | X |

|  | Comparative Preparation Example 11 | Comparative Preparation Example 12 | Comparative Preparation Example 13 | Comparative Preparation Example 14 | Comparative Preparation Example 15 |
|---|---|---|---|---|---|
| Kind of mica | Fluorophlogopite | Fluorophlogopite | Sodium taeniolite | Sodium taeniolite | Fluorophlogopite |
| Aqueous solution for contact | — | — | — | — | citric acid |
| Heat treatment temperature (°C.) | 500 | 1000 | 700 | 500 | 500 |
| End face shape | flat | flat | flat | flat | laminated |
| F mol % (%) (powder F mol number/stoichiometrical F mol number × 100) | 100 | 95 | 90 | 100 | 100 |
| F leaching amount (ppm) | 20 | less than 1 | less than 1 | 42 | 20 |
| K leaching amount (ppm) | 8.7 | less than 1 | less than 1 | 21 | 8.7 |
| Surface activity (t-butanol residue %) | 52 | 96 | 95 | 60 | 99 |
| Whiteness (V value) | 7.9 | 8.9 | 8.9 | 5.6 | 8.0 |
| Stability | X | X | X | X | ○ |
| Overall estimation | X | X | X | X | X |

Then, examples of cosmetics blended with the synthetic mica powder are shown.

The performance of the cosmetics were functionally estimated for five stages by 20 expert panelers regarding the items listed in the following table.

TABLE 12

| Estimation | Extensibility | Adherence | Gloss | Adherence feeling | Smooth feeling in use | Fineness of made-up skin |
|---|---|---|---|---|---|---|
| 1 | extremely poor | extremely poor | none | none | not at all | extremely dirty |
| 2 | poor | poor | less | less | none | dirty |
| 3 | ordinary | ordinary | ordinary | ordinary | ordinary | ordinary |
| 4 | good | good | present | present | smooth | fine |
| 5 | excellent | excellent | extremely high | extremely high | extremely smooth | extremely fine |

The result of the estimation is shown by the following symbols based on the average values obtained form 20 panelers by 5 stage estimation.

◉ ... 4.5–5.0
○ ... 3.5–4.5
Δ ... 2.5–3.5
x ... 1.5–2.5
xx ... 1.0–1.5

EXAMPLE 8

Powder Foundation

The powder foundation X according to the present invention was prepared by each of the following ingredients.

| | (wt %) |
|---|---|
| 1. Titanium oxide | 7 |
| 2. Talc | 20 |
| 3. Muscovite | 3 |
| 4. Synthetic mica powder of preparation Example 10 | 55 |
| 5. Nylon powder | 2 |
| 6. Red iron oxide | 0.5 |
| 7. Yellow iron oxide | 1 |
| 8. Black iron oxide | 0.1 |
| 9. Silicon oil | 1 |
| 10. 2-Ethylhexyl palmitate | 9 |
| 11. Sorbitan sesquioleate | 1 |
| 12. Preservative | 0.3 |
| 13. Perfume | 0.1 |

The ingredients 1–8 were mixed in a Henschel mixer and then the ingredients 9–13 melted and mixed under heating were admixed to the mixture, which was then pulverized in a 5 HP pulverizer (of Hosokawa Micron) and then molded under the pressure of 160 kg/cm² into a pan of 5.3 cm diameter to obtain a powder foundation X according to the present invention.

A powder foundation Y for comparison was prepared in the same procedures as above except for using the identical amount of sericite instead of the synthetic mica powder of the ingredient 4. The results for the functional estimation are shown in the following table.

TABLE 13

| Powder foundation | Extensibility | Adherence | Gloss | Smooth feeling in use | Adherence feeling | Fineness of made-up skin |
|---|---|---|---|---|---|---|
| X (Invention) | ◉ | ◉ | ○ | ○ | ◉ | ◉ |
| Y (Comparison) | ○ | ○ | Δ | Δ | Δ | ○ |

As apparent from the table, it can be seen that the powder foundation X according to the present invention has higher estimation. Further, since the hardness of the foundation X of the present invention was 24 and that of the foundation for comparison was 46, it can be seen that the foundation X according to the present invention shows better moldability.

EXAMPLE 9

Brusher

A brusher X according to the present invention was prepared from each of the following ingredients.

| | (wt %) |
|---|---|
| (1) Talc | 12.6 |
| (2) Sericite | 8.1 |
| (3) Muscovite | 5.0 |
| (4) Synthetic mica powder of Preparation Example 11 | 62.5 |
| (5) Red #226 | 0.4 |
| (6) Titanium mica | 3.0 |
| (7) Squalane | 3.0 |
| (8) 2-Ethylhexyl palmitate | 5.0 |
| (9) Preservative | 0.3 |
| (10) Perfume | 0.2 |

The ingredients (1), (2), (3), (4) and (5) were mixed in a Henschel mixer and the ingredients (7), (8), (9) and (10) melted and mixed under heating were blown to the mixture and further mixed. Then, the resulting mixture was pulverized in a 5 HP pulverizer (of Hosokawa Micron), mixed with addition of the ingredient (6) and then molded under the pressure of 120 kg/cm² into a pan of 4×6 cm to obtain a brush X according to the present invention.

A brusher Y for comparison was prepared in the same procedures as above except for replacing 62.5% by weight of the synthetic mica powder of the ingredient (4) with 20% by weight of sericite and 42.5% by weight of muscovite. The result for the functional estimation are shown in the table below.

TABLE 14

| Brusher | Extensibility | Adherence | Gloss | Smooth feeling in use | Adherence feeling | Fineness of made-up skin |
|---|---|---|---|---|---|---|
| X (Invention) | ○ | ○ | ○ | ○ | ◉ | ◉ |
| Y (Comparison) | Δ | Δ | Δ | Δ | Δ | ○ |

As apparent from the table, it can be seen that the brusher X according to the present invention is excellent in any of the items for the functional estimation. Further, since the hardness of the brusher X according to the present invention was 29, and that for the brusher Y according to the present invention has better moldability. Further, as the result of measuring the outer looking color of the molding product by the Hitachi color analyzer 607, it can seen that the chroma of the brusher according to the present invention was 12.0, and that for the brusher Y for comparison was 10.5. Accordingly, it can be seen that the brusher X according to the present invention has higher saturation and shows clear outer looking color.

EXAMPLE 10

Fancy Powder

The fancy powder X according to the present invention was prepared from each of the following ingredients.

|   | (wt %) |
|---|---|
| (1) Synthetic mica powder of Preparation Example 12 | 95 |
| (2) Talc | 4 |
| (3) Perfume | 1 |
| (4) Iron oxide pigment | Proper amount |

After mixing the ingredients (1), (2) and (4), the ingredients (3) was admixed, which was charged in a container to obtain a fancy powder X according to the present invention.

A fancy powder Y for comparison was prepared in the same procedures as above except for using the identical amount of talc instead of 95% by weight of the synthetic mica powder of the ingredient (1) (accordingly, 99% by weight in total). The samples of each of the fancy powders X and Y preserved for one month in a thermostat at 37° C. and each of the controls (just after the preparation of fancy powders X and Y with the same formulations) were compared for the perfume stability by the functional estimation.

In the case of the fancy powder X according to the present invention, there is no substantial change between the sample after one month preservation and the control. While on the other hand, in the case of the fancy powder Y for comparison, the odor of the sample after one month preservation was remarkably changed as compared with that of the control.

Furthermore, as the result of the measurement for the outer looking color of the molding product by Hitachi Color Analyzer 607, it was found that the chroma of the brusher according to the present invention was 11.5 while the saturation of the brusher for the comparison was 10.5. Accordingly, the brusher X of the present invention has higher chroma and also clear outer looking color.

EXAMPLE 11

Nail enamel

The nail enamel according to the present invention was prepared by each of the following ingredients.

|   | (wt %) |
|---|---|
| (1) Nitrocellulose | 12 |
| (2) Modified alkyd resin | 12 |
| (3) Acetyl tributyl citrate | 5 |
| (4) n-Butyl acetate | 36.4 |
| (5) Ethyl acetate | 6 |
| (6) n-Butyl alcohol | 2 |
| (7) Toluene | 21 |
| (8) Iron oxide pigment | 0.5 |
| (9) Titanium dioxide | 0.1 |

-continued

|   | (wt %) |
|---|---|
| (10) Pearl pigment | 2 |
| (11) Synthetic mica powder in Preparation Example 12 | 2 |
| (12) Organic-modified montmorillonite | 1 |

The ingredients 1-7 (the ingredient 4 was used partially) were dissolved and the ingredient 12 and the remaining portion of the ingredient 4 mixed into a gel-like state was admixed to the solution. Then, the ingredients 8-11 were further admixed and charged in a container to obtain the nail enamel according to the present invention.

A nail enamel Y for comparison was prepared by the same procedures as above except for suing the same amount of sericite instead of the synthetic mica powder of the ingredient 11.

The results of the functional estimation are shown in the following table.

TABLE 15

| Nail enamel | Estimation item | |
|---|---|---|
|   | Extensibility | Wear resistance |
| X (Invention) | O | ⊚ |
| Y (Comparison) | Δ | Δ |

As apparent from the table, it can be seen that the nail enamel X according to the present invention is excellent in any of the items for the functional estimation. Particularly, the wear resistance is remarkable. Furthermore, since the synthetic mica powder is less precipitated as compared with sericite, it has a merit capable of decreasing the amount of the viscosity improver used.

EXAMPLE 12

Emulsion Foundation

The emulsion foundation X according to the present invention was prepared from each of the following ingredients.

|   | (wt %) |
|---|---|
| (1) Stearic acid | 0.4 |
| (2) Isostearic acid | 0.3 |
| (3) Cetyl 2-ethylhexanoate | 4 |
| (4) Liquid paraffin | 11 |
| (5) Polyoxyethylene (10) stearyl ether | 2 |
| (6) Talc | 15 |
| (7) Pigment | 4 |
| (8) Cetyl alcohol | 0.3 |
| (9) Preservative | 0.09 |
| (10) Synthetic mica powder in Preparation Example 13 | 3 |
| (11) Triethanolamine | 0.42 |
| (12) Propylene glycol | 5 |
| (13) Ion exchanged water | 54.19 |
| (14) Perfume | 0.3 |

After over-heating at 85° C., dissolving and mixing the ingredients 1-9, the ingredient 10 was added and uniformly dispersed. Then, a mixture prepared by over-heating, dissolving and mixing the ingredients 11-14 at 85° C. was gradually added thereto and emulsified. After maintaining the temperature upon emulsification for 10 min. and stirring, the resulting emulsion was cooled to 45° C. while stirring. The ingredient 15 was added thereto and cooling under stirring was continued till 35° C. and the product was recovered and charged into a vessel to obtain an emulsion foundation X according to the present invention. An emulsified foundation Y for comparison was prepared in the same manners as above except for using the same amount of talc instead of the synthetic mica powder of the ingredient 10. The results for the functional estimation are shown in the table below.

TABLE 16

| Emulsion foundation | Estimation item | | | | | |
|---|---|---|---|---|---|---|
| | Extensibility | Adherence | Fitness | Gloss | Adherence feeling in use | Fineness of made-up skin |
| X (Invention) | ○ | ○ | ○ | ○ | ◉ | ◉ |
| Y (Comparison) | △ | △ | △ | △ | △ | ○ |

As apparent from the table, the emulsified foundation X according to the present invention is excellent over the foundation Y for comparison. Further, foundation X according to the present invention was also excellent in the aging stability (with no decomposition). Samples prepared from each of emulsion foundations X and Y after preserving for one month in a thermostat at 37° C. and respective controls (emulsion foundations X and Y prepared by the same formulations and just after the preparation) were compared with respect to the perfume stability by the functional estimation. In the case of the emulsion foundation X according to the present invention, there was no substantial difference between the sample and the control after preservation for one month. While on the other hand, in the case of emulsion foundation Y for comparison, the odor of the sample preserved after one month was rather changed as compared with the control.

INDUSTRIAL APPLICABILITY

The synthetic mica powder according to the present invention shows less leaching of fluorine ions and low surface activity. Furthermore, it shows improved hold of oils due to the lamination at the surface of powder. Accordingly, it is possible to obtain cosmetics excellent in extensibility, gloss, adherence and modability, having outer looking color of high chroma and excellent safety and stability by blending such mica powder with cosmetics that could not be obtained with conventional starting powder material such as talc, mica, kaolin, etc.

That is, in the case of blending the synthetic mica powder according to the present invention with foundation, eye shadow, brusher, etc., cosmetics with excellent extensibility, adherence and gloss, as well having smooth feeling in use can be obtained in the case of blending. The dispersibility is satisfactory. Further, since cosmetics having outer looking color of high chroma can be obtained by blending the synthetic mica powder according to the present invention, it is possible to reduce the blending amount of organic pigment which is poor in the light stability and tends to cause discoloration and disodoration. Furthermore, since the catalytic activity of the synthetic mica powder according to the present invention is low, cosmetics with no degradation in perfume or the like and high stability can be obtained. Furthermore, since the synthetic mica powder for use in the present invention shows the fluorine ion leaching amount as low as about 1/100 for that of the usual synthetic mica powder, it can be said that the cosmetics according to the present invention have high safety. The present cosmetics show excellent close bondability to skin and satisfactory sliding property as compared with conventional synthetic mica powder.

What is claimed is:

1. A process for producing a synthetic mica powder in which the mol number of fluorine in the synthetic mica powder is from 75 to 99% of the stoichiometrical composition comprising heating synthetic mica having the stoichiometrical composition heated at 600–1350° C. to yield said synthetic mica powder having a mol number of fluorine from 75 to 99% of the stoichiometrical composition.

2. A process for producing synthetic mica powder in which the end faces of the particles have a laminated shape comprising contacting synthetic mica in which the end faces of the particles have a plane surface with an aqueous solution containing one or more of an acid or a chelating agent to produce said synthetic mica powder in which the end faces of the particles have a laminated shape.

3. A process for producing synthetic mica powder in which the mol number of the fluorine in the synthetic mica is from 75 to 99% of the stoichiometrical composition, and the end faces of the particles have a laminated shape, which process comprises a step of contacting synthetic mica having the stoichiometrical composition and in which the end faces of the particles have a plane surface with an aqueous solution containing one or more of an acid or a chelating agent and a step of heating at 600°–1350° C. said synthetic mica having the stoichiometrical composition and in which the end faces of the particles have a plane surface to produce said synthetic mica powder in which the mol number of the fluorine is from 75 to 99% of the stoichiometrical composition and the end faces of the particles have a laminated shape.

4. The process of claim 1, wherein the heating is at from 900° to 1350° C.

5. The process of claim 3, wherein the heating is at 900° to 1350° C.

6. The process of claim 2, wherein said acid is hydrochloric acid, nitric acid, sulfuric acid, chloric acid, perchloric acid, periodic acid, bromic acid, phosphoric acid, boric acid, carbonic acid, formic acid, acetic acid, acrylic acid, benzoic acid, oxalic acid, malonic acid, succinic acid, glutaric acid, adipic acid, pimelic acid, phthalic acid, lactic acid, maleic acid, tartaric acid, citric acid, glycine, alanine, valine, leucine, tyrosine, thoreonine, serine, proline, triptophane, methionine, cystine, thyroxine, asparagine, glutamic acid, lysine or aliginine.

7. The process of claim 3, wherein said acid is hydrochloric acid, nitric acid, sulfuric acid, chloric acid, perchloric acid, periodic acid, bromic acid, phosphoric acid, boric acid, carbonic acid, formic acid, acetic acid, acrylic acid, benzoic acid, oxalic acid, malonic acid, succinic acid, glutaric acid, adipic acid, pimelic acid, phthalic acid, lactic acid, maleic acid, tartaric acid, citric acid, glycine, alanine, valine, leucine, tyrosine, thoreonine, serine, proline, triptophane, methionine, cystine, thyroxine, asparagine, glutamic acid, lysine or aliginine.

* * * * *

UNITED STATES PATENT AND TRADEMARK OFFICE
CERTIFICATE OF CORRECTION

PATENT NO. : 5,023,065
DATED : June 11, 1991
INVENTOR(S) : Kazuhisa OHNO, et al.

It is certified that error appears in the above-identified patent and that said Letters Patent is hereby corrected as shown below:

Col. 1, line 14, delete "safety", and insert --safe--.

Col. 1, line 29, after "is" insert --a--;
                 delete "minerals", and insert --mineral--.

Col. 3, line 56, delete "ore", and insert --or--.

Col. 4, line 63, delete "cleavage", and insert --cleavages--.

line 65, delete "cleavage", and insert --cleavages--.

Col. 6, line 14, delete "acid" and insert --acids--;
        line 18, delete "acid" and insert --acids--.

Col. 6, line 46, after "invention" insert --is--;
        line 63, delete "obtained".

UNITED STATES PATENT AND TRADEMARK OFFICE
CERTIFICATE OF CORRECTION

PATENT NO. : 5,023,065

DATED : June 11, 1991

INVENTOR(S) : Kazuhisa OHNO, et al.

It is certified that error appears in the above-identified patent and that said Letters Patent is hereby corrected as shown below:

Col. 7, line 5, delete "cleveage", and insert --cleavages--.

Col. 7, line 30, delete "2 mol", and insert --2 mols--.

Col. 9, line 13, delete "ceramics", and insert --ceramic--.

Col. 9, line 55, delete "acid", and insert --acids--.

Col. 9, lines 66, 67, and 68, delete in its entirety.

Col. 14, line 53, delete "result", and insert --results--.

Col. 18, line 58, delete "result", and insert --results--.

UNITED STATES PATENT AND TRADEMARK OFFICE
CERTIFICATE OF CORRECTION

PATENT NO. : 5,023,065
DATED     : June 11, 1991
INVENTOR(S) : Kazuhisa OHNO, et al.

It is certified that error appears in the above-identified patent and that said Letters Patent is hereby corrected as shown below:

Col. 19, line 42, delete "result", and insert --results--.

Col. 21, line 1, after "85°C," insert --and--;

line 4, after "85°C," insert --and--.

Col. 21, line 49, after "dried," insert --and--.

Col. 22, line 20, delete "adcid", and insert --acid--.

Col. 25, line 1, delete "were", and insert --was--.

Col. 29, line 1, delete "manners", and insert --manner--.

Col. 29, line 42, delete "modability", and insert --moldability--.

UNITED STATES PATENT AND TRADEMARK OFFICE
CERTIFICATE OF CORRECTION

PATENT NO. : 5,023,065
DATED : June 11, 1991
INVENTOR(S) : Kazuhisa Ohno, et al.

It is certified that error appears in the above-indentified patent and that said Letters Patent is hereby corrected as shown below:

Col. 29, line 58, delete "disodoration", and insert
--a bad odor--.

Signed and Sealed this

Twenty-eighth Day of September, 1993

Attest:

BRUCE LEHMAN

Attesting Officer

Commissioner of Patents and Trademarks